(12) United States Patent
Fliege et al.

(10) Patent No.: US 9,855,179 B2
(45) Date of Patent: Jan. 2, 2018

(54) RAIL GUIDE HAVING A SECURING UNIT, PATIENT TABLE HAVING A RAIL GUIDE FOR ACCESSORIES, AND METHOD FOR OPERATING A RAIL GUIDE

(71) Applicant: SIEMENS HEALTHCARE GMBH, Erlangen (DE)

(72) Inventors: Fabian Fliege, Kastl (DE); Wolfgang Neuber, Pressath (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/582,933

(22) Filed: May 1, 2017

(65) Prior Publication Data

US 2017/0312159 A1  Nov. 2, 2017

(30) Foreign Application Priority Data

Apr. 29, 2016 (DE) .......................... 10 2016 207 417

(51) Int. Cl.
*A61G 13/10* (2006.01)
*A61G 13/00* (2006.01)
(Continued)

(52) U.S. Cl.
CPC ............. *A61G 13/101* (2013.01); *A47B 1/10* (2013.01); *A47B 13/081* (2013.01); *A61G 13/02* (2013.01);
(Continued)

(58) Field of Classification Search
CPC ........ A61G 7/015; A61G 7/05; A61G 7/0507; A61G 7/0508; A61B 6/04; A61B 6/0407;
(Continued)

(56) References Cited

U.S. PATENT DOCUMENTS 3,336,060 A * 8/1967 Bradford ................ A61G 1/003
403/108
3,426,367 A * 2/1969 Bradford .............. A47C 17/645
403/108
(Continued)

FOREIGN PATENT DOCUMENTS

DE         3007071 A1    9/1980
DE         9012531 U1    11/1990
(Continued)

*Primary Examiner* — Robert G Santos
(74) *Attorney, Agent, or Firm* — Laurence A. Greenberg; Werner H. Stemer; Ralph E. Locher

(57) ABSTRACT

A securable rail guide contains a guide rail, a runner rail arranged in the guide rail and able to travel along the guide rail, and a securing unit which is embodied to fix the runner rail in position in the guide rail in a releasable manner. A locking unit is arranged on the guide rail and is embodied to secure the runner rail in a locked position, and an unlocking unit is arranged on the runner rail. The locking unit and the unlocking unit are parts of the securing unit. The unlocking unit is operatively connected to the locking unit such that an actuation of the unlocking unit releases the runner rail to allow a free movement along the guide rail. This configuration provides a separation of the locking and unlocking mechanisms, as a result of which an independent configuration of the stability of the overall locking mechanism is possible.

11 Claims, 4 Drawing Sheets

(51) Int. Cl.
*A47B 1/10* (2006.01)
*A47B 13/08* (2006.01)
*A61G 13/02* (2006.01)
*F16C 29/10* (2006.01)
*F16C 29/04* (2006.01)

(52) U.S. Cl.
CPC ............ *F16C 29/045* (2013.01); *F16C 29/10* (2013.01); *A61G 13/10* (2013.01); *F16C 2316/10* (2013.01)

(58) Field of Classification Search
CPC ..... A47C 19/005; A47C 19/02; A47C 19/025; A47C 19/04
USPC .... 5/600, 601, 620, 81.1 HS, 943, 625, 627, 5/110–112, 114, 200.1, 201, 202
See application file for complete search history.

(56) References Cited

U.S. PATENT DOCUMENTS

| | | | |
|---|---|---|---|
| 4,312,500 A | 1/1982 | Janssen | |
| 5,199,060 A | 3/1993 | Kato | |
| 5,533,844 A * | 7/1996 | Ekleberry | B23Q 1/601 108/143 |
| 6,843,182 B2 | 1/2005 | Torcheboeuf | |
| 6,857,147 B2 * | 2/2005 | Somasundaram | A61B 6/102 5/600 |
| 6,986,179 B2 * | 1/2006 | Varadharajulu | A61B 6/0457 378/209 |
| 2004/0060482 A1 * | 4/2004 | Torcheboeuf | A61G 13/02 108/20 |
| 2004/0098804 A1 * | 5/2004 | Varadharajulu | A61B 6/0457 5/611 |
| 2004/0133983 A1 | 7/2004 | Newkirk et al. | |
| 2004/0172756 A1 * | 9/2004 | Somasundaram | A61B 6/102 5/600 |
| 2005/0004470 A1 | 1/2005 | Camus et al. | |
| 2010/0278588 A1 | 11/2010 | Jaekel | |

FOREIGN PATENT DOCUMENTS

| | | |
|---|---|---|
| DE | 102004001774 A1 | 7/2004 |
| DE | 20308606 U1 | 11/2004 |
| DE | 202009006443 U1 | 10/2010 |
| DE | 10196489 B3 | 5/2015 |

* cited by examiner

RAIL GUIDE HAVING A SECURING UNIT, PATIENT TABLE HAVING A RAIL GUIDE FOR ACCESSORIES, AND METHOD FOR OPERATING A RAIL GUIDE

CROSS-REFERENCE TO RELATED APPLICATION

This application claims the priority, under 35 U.S.C. §119, of German application DE 10 2016 207 417.2, filed Apr. 29, 2016; the prior application is herewith incorporated by reference in its entirety.

BACKGROUND OF THE INVENTION

Field of the Invention

The invention relates to a securable rail guide having a guide rail, a runner rail that is able to travel along the guide rail, and a securing unit which can lock the runner rail in a fixed position in the guide rail in a releasable manner. A patient table having a securable rail guide of this type for accessories and a method for operating a securable rail guide are also disclosed.

Accessory rails which serve for receiving and storing accessory parts and equipment that are required for the treatment of a patient are often mounted on the long sides of patient tables or couches used in medical engineering applications. Also attached thereto are operator control modules by way of which a medical system may be operated and controlled by a user. For certain applications it is also possible to attach a radiation protection shield to the side-mounted accessory rails in order to protect the user's body against undesirable X-ray radiation.

In certain applications, in angiography for example, the side-mounted accessory rails are displaceable in terms of their position. This has the advantage that the parts and modules attached to the rails for use by the user may be moved into the most favorable position for him or her. For this purpose a retaining function (e.g. securing function) of the accessory rail is required. The retaining function is required to ensure that the accessory rail maintains the desired position in an unactuated state. In order to change the position of the accessory rail, an unlocking function is actuated by the user. Only then can the accessory rail be moved to a different position. As soon as the user releases the unlocking function once more, the position of the accessory rail is retained or secured by a locking mechanism.

In the case of patient tables having a tilt function, the patient can be moved from a horizontal position to an angled position. At an inclined attitude, the accessory rail is also moved into an angled position. A downhill force dependent on tilt angle and accessory load acts on the locking mechanism of the accessory rail and must be absorbed by the locking mechanism. A tilting movement is possible in two directions of rotation. The forces may be considerable due to large tilt angles and high accessory loads.

In the case of patient tables known from real-world practice, the unlocking mechanism is coupled directly to the locking mechanism. For this reason the force flow when the accessory rail is retained in a fixed position always has an effect also on the unlocking mechanism, which is subjected to severe load at high retaining forces. Furthermore, in the case of known solutions, the locking positions arranged on the stationary part of the patient table are also always visible and accessible when the accessory rail is displaced. This is not ideal and is undesirable from the point of view of hygiene.

A rail guide having an accessory rail for patient tables is known for example from German utility model application DE 203 08 606 U1.

SUMMARY OF THE INVENTION

It is the object of the invention to disclose a securable rail guide, a patient table having a securable rail guide, and a method for operating a securable rail guide, the unlocking mechanism of which is subjected to a load exerting a minimum possible force and in which the parts of the locking and unlocking mechanisms are not directly visible and accessible.

The addressed object is achieved according to the invention by the securable rail guide, the patient table and the method of the independent claims. Advantageous developments are set forth in the dependent claims.

According to the invention, the problem of the high retaining force is solved by a separation of the force flow from the locking to the unlocking mechanism. The retaining force is not transmitted to the unlocking mechanism via a locking element, because the locking mechanism acts directly on the movable runner rail of the rail guide. The mechanism for unlocking is only indirectly coupled to the locking mechanism. In this case the unlocking mechanism acts on the locking mechanism and releases the latter's connection to the runner rail. The actuation of the unlocking mechanism moves the locking mechanism out of engagement and allows a free movement of the runner rail (e.g. locked state released). As a result of the unlocking mechanism being released, the locking mechanism is reactivated in order to secure the runner rail in a locked position.

A rail guide is composed of two rails, namely a guide rail and a runner rail, which are displaceable relative to one another and on one of which a part requiring to be moved may be mounted.

The invention affords the advantage that a separation of locking and unlocking mechanism is realized, as a result of which an independent configuration of the stability of the overall locking mechanism is made possible. The unlocking mechanism may be configured with less stability, since it is outside of the force flow required for retaining the rail in its position. A stable locking mechanism is necessary for retaining a great force and is actuated by a less stable unlocking mechanism in order to be released.

Furthermore, the described separation enables the rail locking arrangement to be implemented in a concealed embodiment. No mechanism is visible at any displacement position. All components required for the locking arrangement are located in the concealed region, which affords a great advantage in terms of hygiene and is also favorable visually.

The separation of locking and unlocking mechanism enables the function to be realized through the use of preassembled modules which, for example, are easy to mount in a patient table and are also easily replaceable in the event of damage or contamination.

The invention claims a securable rail guide having a guide rail, having a runner rail arranged in the guide rail and able to travel along the guide rail, and having at least one securing unit which fixes the runner rail in position in the guide rail in a releasable manner. The rail guide additionally contains a locking unit which is arranged on the guide rail and which secures the runner rail in a locked position, and an unlocking unit arranged on the runner rail. The locking unit and the unlocking unit are parts of the securing unit and the unlocking unit is operatively connected to the locking unit in such a way that an actuation of the unlocking unit releases the runner rail to allow its free movement along the guide rail, i.e. releases the locked state.

In a development, the rail guide has a lever of the locking unit, which lever fixes the runner rail in a locked position.

In a further embodiment variant, the rail guide contains a locking plate or locking panel perforated with holes, which is arranged along the runner rail and connected to the latter, wherein a lug of the lever latches into a hole in order to lock the runner rail in position and arrests the movement of the rail guide.

In a development, the rail guide has a spring element in the locking unit, which spring element latches the lug of the lever into the holes of the locking plate or locking panel, i.e. the lug engages in one of the holes.

In a further embodiment, the rail guide has a torsion bar arranged along the runner rail, which torsion bar, when rotated about its longitudinal axis, moves the lever of the locking unit in such a way that the locked state of the runner rail is released, i.e. the runner rail is able to be moved along the guide rail.

In a further embodiment, the cross-section of the torsion bar is embodied as a circular segment, wherein an edge of the circular segment-shaped torsion bar holds the lever of the locking unit in an unlocked position.

In a development, a pressure roller to which pressure is applied by the torsion bar during the unlocking action is arranged in the lever, the axis of rotation of the pressure roller being aligned in such a way that when the runner rail is moved in the unlocked state of the securing unit, the torsion bar sets the pressure roller into rotation.

In a further embodiment, the guide rail has a plurality of bearing rollers on which the runner rail can be moved along the guide rail.

In addition, there is an unlocking lever which is operatively connected to the torsion bar and with the aid of which a user can unlock the securing unit, i.e. can rotate the torsion bar.

In a further embodiment variant, two or more locking units may be arranged spaced apart at a distance from one another, which locking units can be unlocked simultaneously by the unlocking unit.

The invention also claims a patient table having a tabletop and preferably a stretcher board, wherein a rail guide according to the invention is arranged in the longitudinal direction of the tabletop for the purpose of storing or mounting accessories.

The invention furthermore claims a method for operating a securable rail guide, wherein a locked state of a runner rail arranged so as to be movable in a guide rail is released in that a locking unit connected to the guide rail releases the locked state by an actuation of an unlocking unit connected to the runner rail. This enables the runner rail to be moved along the guide rail. The parking brake, so to speak, is released.

Other features which are considered as characteristic for the invention are set forth in the appended claims.

Although the invention is illustrated and described herein as embodied in a rail guide having a securing unit, a patient table having a rail guide for accessories, and a method for operating a rail guide, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF AN EXEMPLARY EMBODIMENT

Figure 1:
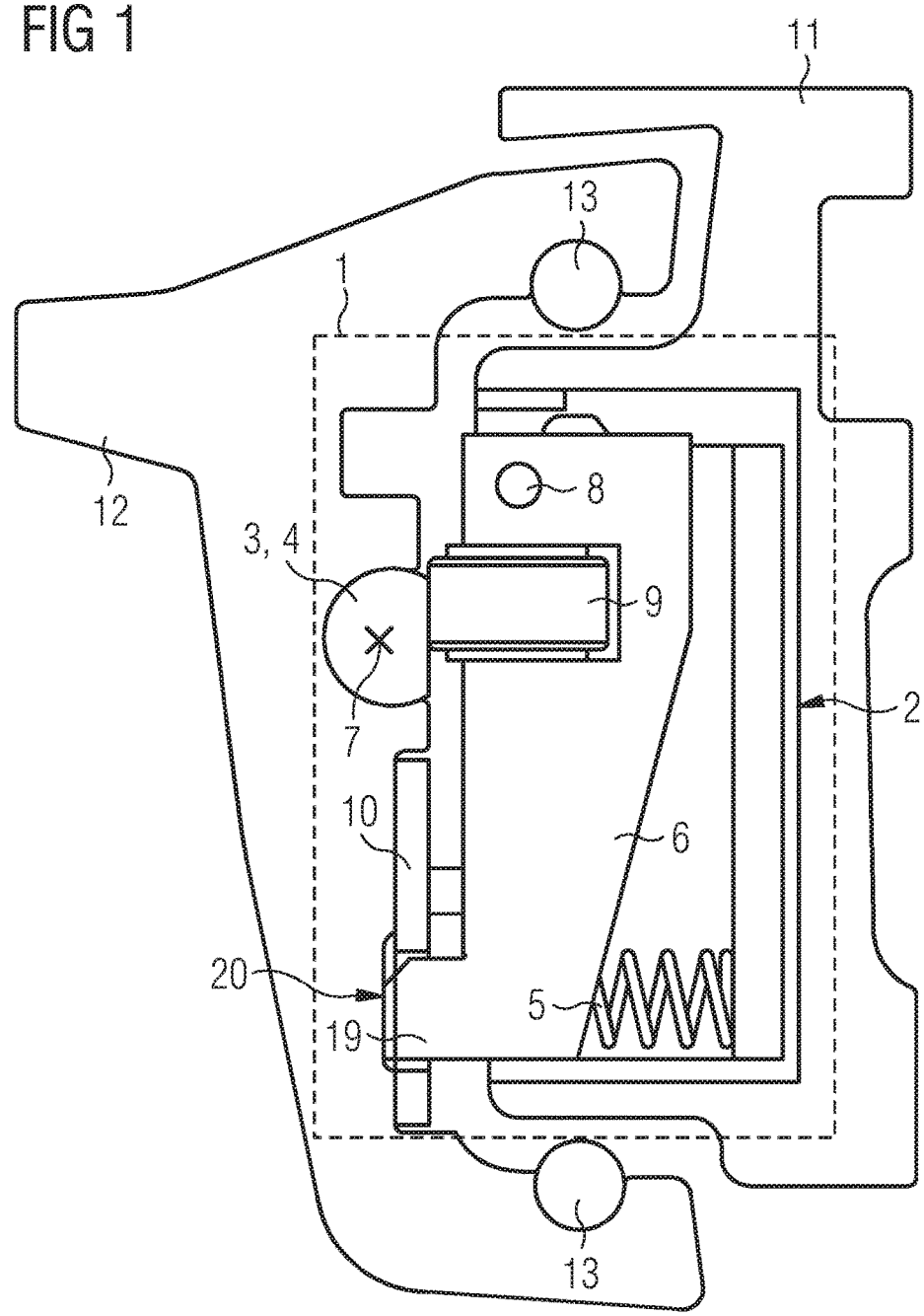
FIG. 1 is a diagrammatic, sectional view of a securable rail guide in a locked state according to the invention.

Referring now to the figures of the drawings in detail and first, particularly to FIG. 1 thereof, there is shown a cross-section of a securing unit 1 of a rail guide in a locked state. To that end, the securing unit 1 has a locking unit 2 and an unlocking unit 3 and has the function of a parking brake for a runner rail 12 that is movable along a guide rail 11. The guide rail 11 is usually permanently mounted on a device and the runner rail 12 is able to move relative to the guide rail 11 and to the device.

The locking unit 2 is mounted on or in the guide rail 11 (or a locking panel) and is able to secure the runner rail 12 in a locked position by a locking plate 10 arranged along the runner rail 12. To that end, the locking plate 10, similarly to a patterned perforated plate, possesses holes 20 into which one or more lugs 19 of a pivotable lever 6 of the locking unit 2 can latch ("engage"). With the aid of a spring element 5, embodied for example as a spiral spring, pressing against the lever 6, the lug 19 is pressed into the hole 20. The lever 6 is able to pivot about the axis of rotation 8. A pressure roller 9 in the lever 6, the axis of rotation of the pressure roller 9 being aligned roughly in the longitudinal direction of the lever 6, serves for interacting with the unlocking unit 3.

The unlocking unit 3, which is mounted on the runner rail 12, serves for unlocking the locking unit 2. The unlocking unit 3 contains a torsion bar 4 which is arranged in the longitudinal direction of the runner rail 12 and which is mounted so as to be rotatable about its longitudinal axis 7 by an unlocking lever (not shown).

The runner rail 12 can be moved on the bearing rollers (not shown) of the guide rail 11 on the guide wires 13 arranged in the longitudinal direction of the runner rail 12.

Figure 2:
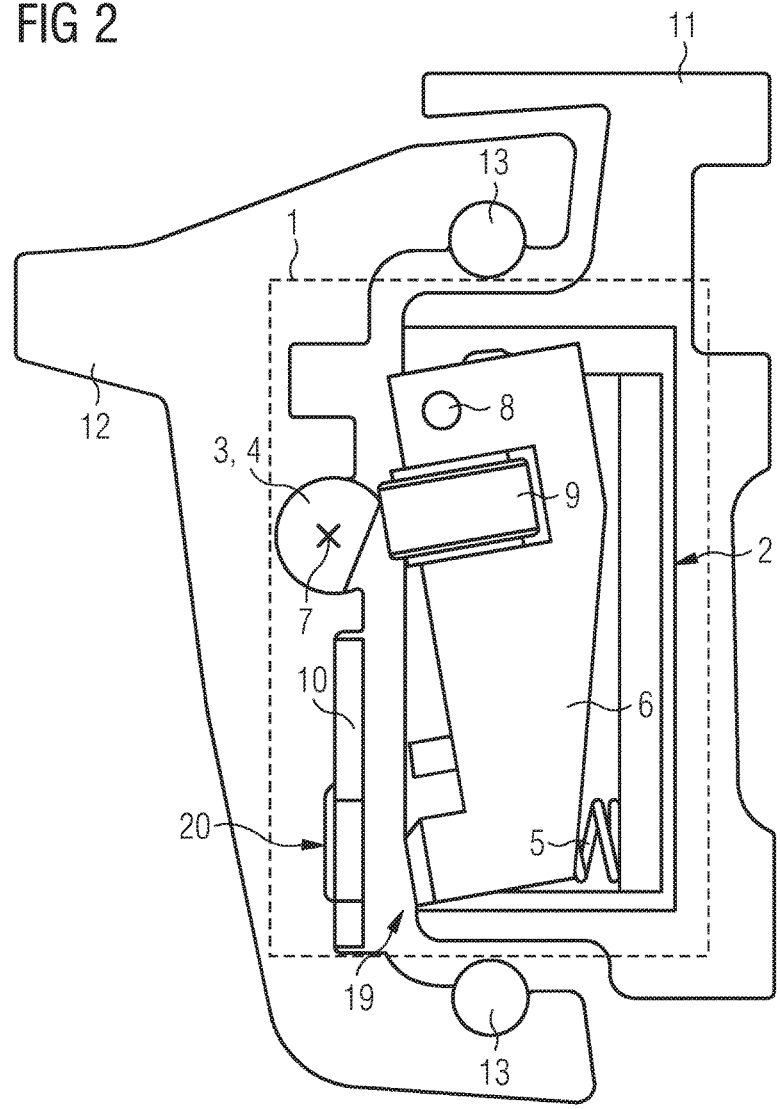
FIG. 2 is a sectional view of the securable rail guide in an unlocked state.

FIG. 2 shows the cross-section of a securable rail guide according to FIG. 1 in an unlocked state. To that end, a torsion bar 4 is rotated about the longitudinal axis 7 out of its locking position into the unlocking position. Because the torsion bar 4 is a circular segment in cross-section, the rotational movement results in a thus formed edge of the torsion bar 4 pressing directly onto the pressure roller 9 of the lever 6 of the locking unit 2. This causes the lever 6 to be pivoted about its axis of rotation 8 and the lug 19 at the tip of the lever 6 is withdrawn from the hole 20, as a result of which the locked state of the runner rail 12 is released and a movement into or out of the image plane of FIG. 2 is made possible.

Figure 3:
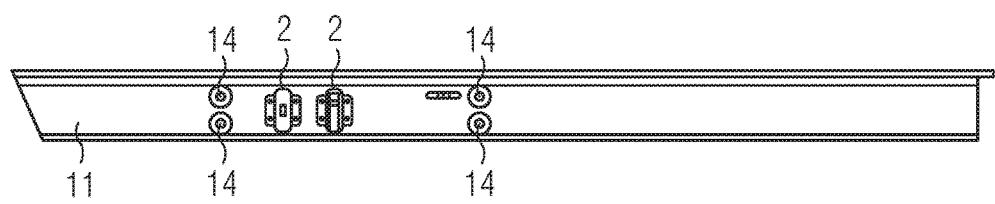
FIG. 3 is a side view of the guide rail having two locking units.

FIG. 3 shows a side view of the guide rail 11 having two locking units 2 arranged therein. In this arrangement, the lugs (not visible) of the locking units 2 are embodied at different heights so that they can engage into different rows of holes in a locking plate. A play of the runner rail with respect to the guide rail 11 is avoided as a result. Also to be seen are the bearing rollers 14 for supporting and moving the runner rail.

Figure 4:
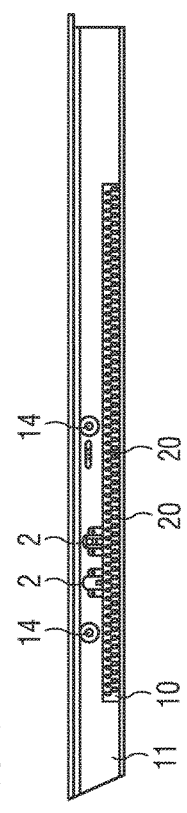
FIG. 4 is a side view of the guide rail having two locking units and a locking plate or locking panel.

FIG. 4 shows a side view of the guide rail 11 having the two locking units 2 according to FIG. 3. The locking plate 10 of the runner rail is also shown. The two-row hole pattern with the holes 20 is clearly to be seen in the locking plate 10.

Figure 5:
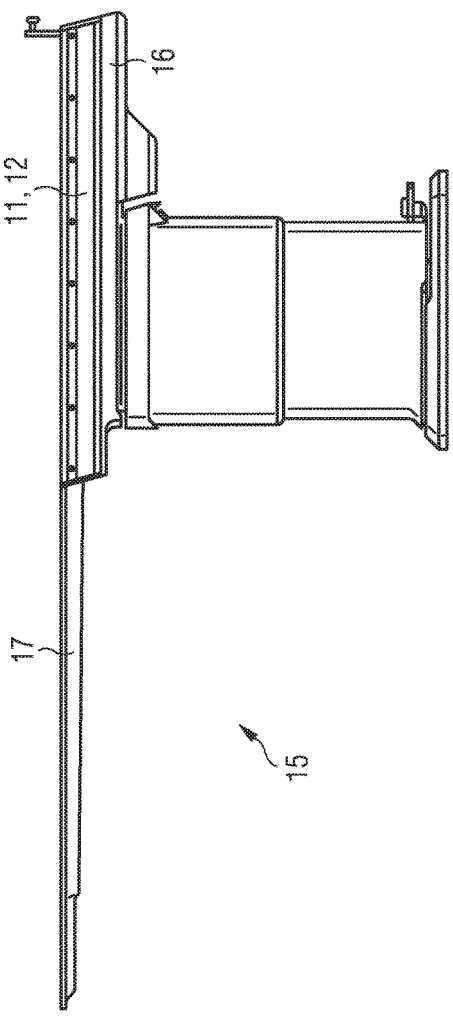
FIG. 5 is a side view of a patient table having the rail guide for accessories.

FIG. 5 shows a side view of a patient table 15 having a rail guide for storing accessories. The guide rail 11 with the runner rail 12 arranged so as to be movable therein is mounted along the tabletop 16 or, as the case may be, the superstructure or longitudinal carriage. Accessory parts (not shown) can be mounted or inserted into the runner rail 12. The stretcher board 17 for supporting a patient is located on the tabletop 16.

Figure 6:
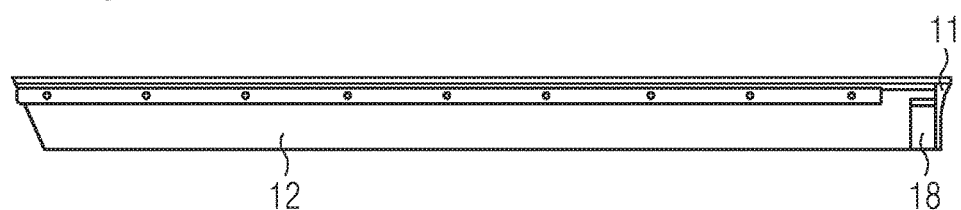
FIG. 6 is a side view of the rail guide of a patient table in a central position.
Figure 7:
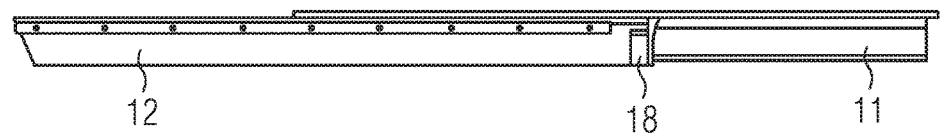
FIG. 7 is a side view of the rail guide of the patient table in a head-end position.
Figure 8:
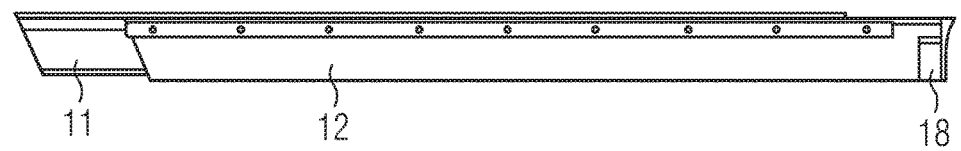
FIG. 8 is a side view of the rail guide of the patient table in a foot-end position.

FIG. 6 to FIG. 8 show the rail guide according to FIG. 3 to FIG. 5 in different positions. Clearly to be seen are the guide rail 11 and the runner rail 12 as well as the unlocking lever 18 for rotating the torsion bar (not visible). It is worth noting that the securing unit is not open or accessible in any position. FIG. 6 shows the runner rail 12 in a central position, FIG. 7 in a head-end position, and FIG. 8 in a foot-end position.

Although the invention has been illustrated and described in greater detail on the basis of the exemplary embodiments, the invention is not limited by the disclosed examples and other variations may be derived therefrom by the person skilled in the art without leaving the scope of protection of the invention.

The following is a summary list of reference numerals and the corresponding structure used in the above description of the invention:
1 Securing unit
2 Locking unit
3 Unlocking unit
4 Torsion bar
5 Spring element
6 Lever
7 Longitudinal axis of the torsion bar 4
8 Axis of rotation of the lever 6
9 Pressure roller
10 Locking plate
11 Guide rail
12 Runner rail
13 Guide wire
14 Bearing roller
15 Patient table
16 Tabletop
17 Stretcher board
18 Unlocking lever
19 Lug of the lever 6
20 Hole of the locking plate 10

The invention claimed is:
1. A securable rail guide, comprising:
a guide rail;
a runner rail disposed in said guide rail and movable along said guide rail; and
at least one securing unit being embodied to fix said runner rail in position in said guide rail in a releasable manner, said at least one securing unit containing:
a locking unit disposed on said guide rail and embodied to secure said runner rail in a locked position, said locking unit having a lever embodied to fix said runner rail in position; and
an unlocking unit disposed on said runner rail, said unlocking unit being operatively connected to said locking unit in such a way that an actuation of said unlocking unit releases said runner rail allowing its free movement along said guide rail.

2. The securable rail guide according to claim 1,
further comprising a locking plate or locking panel having perforated holes formed therein and being disposed along said runner rail and connected to said runner rail; and
wherein said lever has at least one lug which latches into one of said holes in order to secure said runner rail in the locked position.

3. The securable rail guide according to claim 2, wherein said locking unit has a spring element embodied to latch said at least one lug of said lever into one of said holes of said locking plate.

4. The securable rail guide according to claim 1, further comprising a torsion bar disposed along said runner rail and said torsion bar, when rotated about its longitudinal axis, is embodied to move said lever of said locking unit such that a locked state of said runner rail is released.

5. The securable rail guide according to claim 4, wherein a cross-section of said torsion bar is embodied as a circular segment-shaped torsion bar, wherein said circular segment-shaped torsion bar having an edge for holding said lever of said locking unit in an unlocked position.

6. The securable rail guide according to claim 4, further comprising a pressure roller disposed in said lever and to which pressure is applied by said torsion bar during an unlocking action, and an axis of rotation of said lever is aligned in such a way that when said runner rail is moved in an unlocked state of said securing unit, said torsion bar rotates said pressure roller.

7. The securable rail guide according to claim 1, wherein said guide rail has a plurality of bearing rollers disposed in such a way that said runner rail is able to travel along said guide rail on said bearing rollers.

8. The securable rail guide according to claim 4, further comprising an unlocking lever being operatively connected to said torsion bar and by means of said unlocking lever said at least one securing unit can be unlocked by a user.

9. The securable rail guide according to claim 1, wherein said locking unit is one of at least two locking units which are disposed spaced apart at a distance from one another and which can be unlocked simultaneously by said unlocking unit.

10. A patient table, comprising:
a tabletop; and
a rail guide for storing accessories and disposed in a longitudinal direction of said tabletop, said rail guide containing:
a guide rail;
a runner rail disposed in said guide rail and movable along said guide rail;

at least one securing unit being embodied to fix said runner rail in position in said guide rail in a releasable manner, said at least one securing unit containing:
  a locking unit disposed on said guide rail and embodied to secure said runner rail in a locked position, said locking unit having a lever embodied to fix said runner rail in position; and
  an unlocking unit disposed on said runner rail, said unlocking unit being operatively connected to said locking unit in such a way that an actuation of said unlocking unit releases said runner rail allowing its free movement along said guide rail.

11. A method for operating a securable rail guide, which comprises the steps of:
  forming the securable rail guide with a guide rail, a runner rail disposed in the guide rail and movable along the guide rail, and at least one securing unit being embodied to fix the runner rail in position in the guide rail in a releasable manner, the at least one securing unit containing a locking unit disposed on the guide rail and embodied to secure the runner rail in a locked position and an unlocking unit disposed on the runner rail, the unlocking unit being operatively connected to the locking unit in such a way that an actuation of the unlocking unit releases the runner rail allowing its free movement along the guide rail, the locking unit further having a lever embodied to fix the runner rail in position; and
  releasing a locked state of the runner rail disposed so as to be movable in the guide rail in that the locking unit connected to the guide rail releases the locked state by means of an actuation of the unlocking unit connected to the runner rail.

* * * * *